US00PP22735P2

(12) United States Plant Patent
Barends

(10) Patent No.: US PP22,735 P2
(45) Date of Patent: May 15, 2012

(54) ***PELARGONIUM* PLANT NAMED 'FIPELMASRED'**

(50) Latin Name: *Pelargonium×hortorum*
Varietal Denomination: Fipelmasred

(75) Inventor: Eveline Barends, De Lier (NL)

(73) Assignee: Fides B.V., De Lier (NL)

( * ) Notice: Subject to any disclaimer, the term of this patent is extended or adjusted under 35 U.S.C. 154(b) by 4 days.

(21) Appl. No.: 12/925,605

(22) Filed: Oct. 25, 2010

(51) Int. Cl.
*A01H 5/00* (2006.01)

(52) U.S. Cl. ..... Plt./330

(58) Field of Classification Search ..... Plt./325, Plt./330
See application file for complete search history.

*Primary Examiner* — Susan McCormick Ewoldt
(74) *Attorney, Agent, or Firm* — C. A. Whealy

(57) ABSTRACT

A new and distinct cultivar of *Pelargonium* plant named 'Fipelmasred', characterized by its upright and somewhat outwardly spreading growth habit; rounded plant habit; freely basal branching habit; vigorous growth habit; early and freely flowering habit; semi-double dark red-colored flowers; and good garden performance.

1 Drawing Sheet

Botanical designation: *Pelargonium×hortorum*.
Cultivar denomination: 'FIPELMASRED'.

BACKGROUND OF THE INVENTION

The present invention relates to a new and distinct cultivar of *Pelargonium* plant, botanically known as *Pelargonium×hortorum*, commercially referred to as Zonal Geranium and hereinafter referred to by the name 'Fipelmasred'.

The new *Pelargonium* plant is a product of a planned breeding program conducted by the Inventor in De Lier, The Netherlands. The objective of the breeding program is to create new vigorous, freely-branching and freely-flowering *Pelargonium* plants that have good high temperature performance.

The new *Pelargonium* plant originated from a cross-pollination made by the Inventor in September, 2006 in De Lier, The Netherlands of *Pelargonium×hortorum* 'Fipelsumtrur', disclosed in U.S. Plant Pat. No. 21,277, as the female, or seed, parent with a proprietary selection of *Pelargonium×hortorum* identified as code number 04-003-056, not patented, as the male, or pollen, parent. The new *Pelargonium* plant was discovered and selected by the Inventor as a single flowering plant from within the progeny of the stated cross-pollination in a controlled greenhouse environment in De Lier, The Netherlands, in March, 2007.

Asexual reproduction of the new *Pelargonium* plant by vegetative terminal cuttings in a controlled greenhouse environment in De Lier, The Netherlands, since July, 2007, has shown that the unique features of this new *Pelargonium* plant are stable and reproduced true to type in successive generations.

SUMMARY OF THE INVENTION

Plants of the new *Pelargonium* have not been observed under all possible environmental conditions. The phenotype may vary somewhat with variations in environment conditions such as temperature and light intensity without, however, any variance in genotype.

The following traits have been repeatedly observed and are determined to be the unique characteristics of 'Fipelmasred'.

These characteristics in combination distinguish 'Fipelmasred' as a new and distinct cultivar of *Pelargonium* plant:

1. Upright and somewhat outwardly spreading growth habit; rounded plant habit.
2. Freely basal branching habit.
3. Vigorous growth habit.
4. Early and freely flowering habit.
5. Semi-double dark red-colored flowers.
6. Good garden performance.

Plants of the new *Pelargonium* differ primarily from plants of the female parent, 'Fipelsumtrur', in flower color. In addition, plants of the new *Pelargonium* are more vigorous than plants of 'Fipelsumtrur'.

Plants of the new *Pelargonium* differ primarily from plants of the male parent selection in growth habit and uniformity as plants of the new *Pelargonium* are more vigorous and more uniform than plants of the male parent selection.

Plants of the new *Pelargonium* can be compared to plants of *Pelargonium×hortorum* 'Fisrored', disclosed in U.S. Plant Pat. No. 12,917. In side-by-side comparisons conducted in De Lier, The Netherlands, plants of the new *Pelargonium* differed from plants of 'Fisrored' primarily in plant habit as plants of the new *Pelargonium* were more rounded than plants of 'Fisrored'. In addition, leaves of plants of the new *Pelargonium* had a more distinct zonation pattern than leaves of plants of 'Fisrored'.

BRIEF DESCRIPTION OF THE PHOTOGRAPH

The accompanying colored photograph illustrates the overall appearance of the new *Pelargonium* plant showing the colors as true as it is reasonably possible to obtain in colored reproductions of this type. Colors in the photograph may differ slightly from the color values cited in the detailed botanical description which accurately describe the colors of the new *Pelargonium* plant.

The photograph comprises a side perspective view of a typical flowering plant of 'Fipelmasred' grown in a container.

DETAILED BOTANICAL DESCRIPTION

The aforementioned photograph and following observations, measurements and values describe plants grown during the spring in 17-cm containers in De Lier, The Netherlands in a glass-covered greenhouse and under conditions which closely approximate commercial *Pelargonium* production. During the production of the plants, day temperatures ranged from 17° C. to 18° C. and night temperatures ranged from 14° C. to 16° C. Plants were 12 and 13 weeks old when the photograph and the description, respectively, were taken. In the detailed description, color references are made to The Royal Horticultural Society Colour Chart, 2007 Edition, except where general terms of ordinary dictionary significance are used.

Botanical classification: *Pelargonium×hortorum* 'Fipelmasred'.

Parentage:

*Female, or seed, parent*.—*Pelargonium×hortorum* 'Fipelsumtrur', disclosed in U.S. Plant Pat. No. 21,277.

*Male or pollen parent*.—Proprietary selection of *Pelargonium×hortorum* identified as code number 04-003-056, not patented.

Propagation:

*Type*.—By vegetative terminal cuttings.

*Time to initiate roots, summer*.—About four days at temperatures of 22° C.

*Time to initiate roots, winter*.—About seven days at temperatures of 22° C.

*Time to produce a rooted young plant, summer*.—About 16 days at temperatures of 22° C. to 30° C.

*Time to produce a rooted young plant, winter*.—About 21 days at temperatures of 20° C. to 25° C.

*Root description*.—Medium in thickness, fibrous; whitish grey in color.

*Rooting habit*.—Moderate branching, medium density.

Plant description:

*Plant form and habit*.—Upright and somewhat outwardly spreading growth habit; rounded and uniformly mounded plant habit; densely foliated.

*Growth and branching habit*.—Vigorous growth habit; freely basal branching habit with about eight to ten basal branches developing per plant.

*Plant height, to top of umbels*.—About 24 cm.

*Plant height, to top of foliar plane*.—About 14 cm.

*Plant width*.—About 37 cm.

*Lateral branches*.—Length: About 2 cm to 12 cm. Diameter: About 5 mm to 8 mm. Internode length: About 1 cm to 3 cm. Texture: Pubescent. Strength: Moderately strong. Color: Close to 144A.

Foliage description:

*Arrangement*.—Alternate; simple.

*Length* (*including petiole*).—About 7 cm to 8 cm.

*Width*.—About 12 cm to 13 cm.

*Shape*.—Orbicular.

*Apex*.—Acute.

*Base*.—Cordate.

*Margin*.—Crenate.

*Venation pattern*.—Palmate.

*Texture, upper surface*.—Smooth, glabrous.

*Texture, lower surface*.—Slightly pubescent.

*Color*.—Developing leaves, upper surface: Close to N137A. Developing leaves, lower surface: Close to 147B. Fully expanded leaves, upper surface: Close to N137B; venation, close to N137B. Fully expanded leaves, lower surface: Close to 147B; venation, close to 146C. Zonation pattern: Location: Center of the leaf. Width: About 2 cm. Color: Close to 147A.

*Petiole*.—Length: About 9 cm to 10 cm. Diameter: About 2 mm to 3 mm. Texture, upper and lower surfaces: Pubescent. Color, upper and lower surfaces: Close to 146A.

Flower description:

*Flower arrangement*.—Semi-double rotate flowers arranged in rounded hemispherical umbels arising from apical leaf axils; umbels displayed above the foliage on strong peduncles; flowers face upright to outward.

*Fragrance*.—None detected.

*Quantity of flowers*.—Freely flowering habit; about nine to eleven umbels develop per plant each umbel with about 61 to 67 flowers and flower buds.

*Flowering season*.—In The Netherlands, flowering is continuous from late spring until frost in the autumn; early flowering habit, plants begin flowering about six to eight weeks after planting.

*Flower longevity*.—Depending on environmental conditions, individual flowers last about 2 to 14 days on the plant; flowers persistent.

*Umbel height*.—About 8 cm to 9 cm.

*Umbel diameter*.—About 12 cm to 13 cm.

*Flower diameter*.—About 5 cm.

*Flower depth* (*height*).—About 2 cm.

*Flower buds*.—Length: About 1.8 cm. Diameter: About 8 mm. Shape: Globular to elliptical. Color: Close to 45C.

*Petals*.—Quantity per flower: About eight to nine. Length: About 2.5 cm to 2.8 cm. Width: About 2 cm. Shape: Spatulate to obovate. Apex: Obtuse. Base: Attenuate. Margin: Entire. Texture, upper and lower surfaces: Smooth, glabrous; velvety. Color: When opening, upper and lower surfaces: Close to 45C. Fully opened, upper and lower surfaces: Close to 45B; color becoming closer to 45A with development.

*Petaloids*.—Quantity per flower: If present, typically only one. Length: About 1 cm to 1.5 cm. Width: About 1 mm to 3 mm. Shape: Irregularly shaped; obovate to irregularly oblanceolate. Apex: Obtuse. Base: Attenuate. Margin: Entire. Texture, upper and lower surfaces: Smooth, glabrous; velvety. Color: When opening, upper and lower surfaces: Close to 45B. Fully opened, upper and lower surfaces: Close to 45B.

*Sepals*.—Quantity per flower: Five, arranged in a single whorl. Length: About 1 cm. Width: About 3 mm. Shape: Lanceolate to ovate. Apex: Acute. Base: Lobate to truncate. Margin: Entire. Texture, upper and lower surfaces: Densely pubescent. Color, upper and lower surfaces: Close to 146C to 146D.

*Peduncle* (*umbel stem*).—Length: About 21 cm to 24 cm. Diameter: About 4 mm to 5 mm. Strength: Strong. Angle: Erect to about 30° C. from vertical. Texture: Pubescent. Color: Close to 146A.

*Pedicel* (*individual flower stem*).—Length: About 3 cm. Diameter: About 1 mm to 2 mm. Strength: Moderately strong. Angle: Erect to about 60° C. from vertical. Texture: Pubescent. Color: Close to 146C.

*Reproductive organs*.—Androecium: Stamen quantity per flower: About one to six. Filament length: About 6 mm to 8 mm. Filament color: Close to NN155D. Anther length: About 2 mm to 3 mm. Anther shape: Oblong. Anther color: Close to 172A. Pollen amount: Moderate. Pollen color: Close to 33B. Gynoecium: Pistil quantity per flower: One. Pistil length: About 9 mm to 12 mm. Stigma shape: Tapering; reflexed. Stigma color: Close to 172A. Style length: About 4 mm to 5 mm. Style color: Close to 172A. Ovary color: Close to 146A.

*Fruits/seeds*.—Fruit and seed development have not been observed.

Disease/pest resistance: Plants of the new *Pelargonium* have not been observed to be resistant to pathogens and pests common to *Pelargoniums*.

Garden performance: Plants of the new *Pelargonium* have been observed to tolerate rain, wind, and temperatures ranging from about 0° C. to about 45° C. and have demonstrated good garden performance.

It is claimed:

1. A new and distinct *Pelargonium* plant named 'Fipelmasred' as illustrated and described.

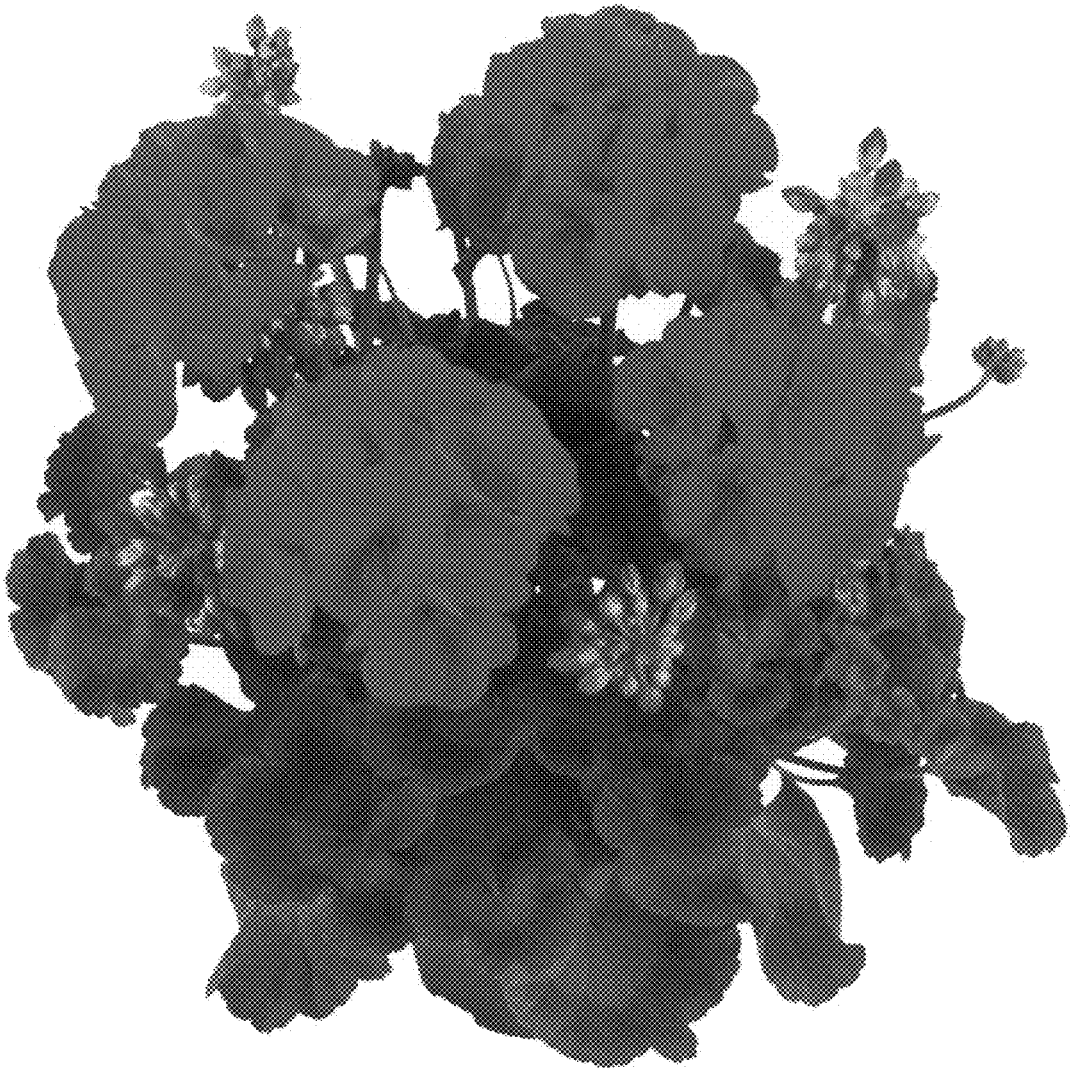

* * * * *